US012755100B2

(12) United States Patent
Clarke et al.

(10) Patent No.: US 12,755,100 B2
(45) Date of Patent: Oct. 6, 2026

(54) COMPUTING N-DIMENSIONAL SENTIMENT USING A LARGE LANGUAGE MODEL

(71) Applicant: Compass Pathfinder Limited, Altrincham (GB)

(72) Inventors: Patrick Clarke, Philadelphia, PA (US); Robert F. Dougherty, Redwood City, CA (US); Gregory A. Ryslik, Westerville, OH (US); Carly Leininger, Altrincham (GB)

(73) Assignee: Compass Pathfinder Limited, Altrincham (GB)

( * ) Notice: Subject to any disclaimer, the term of this patent is extended or adjusted under 35 U.S.C. 154(b) by 110 days.

(21) Appl. No.: 18/274,387

(22) PCT Filed: Jul. 25, 2023

(86) PCT No.: PCT/US2023/070896
§ 371 (c)(1),
(2) Date: Jul. 26, 2023

(87) PCT Pub. No.: WO2024/026283
PCT Pub. Date: Feb. 1, 2024

(65) Prior Publication Data
US 2025/0013830 A1 Jan. 9, 2025

Related U.S. Application Data

(63) Continuation of application No. PCT/US2023/070857, filed on Jul. 24, 2023.
(Continued)

(51) Int. Cl.
*G10L 25/63* (2013.01)
*G06F 40/279* (2020.01)
(Continued)

(52) U.S. Cl.
CPC ............ *G06F 40/30* (2020.01); *G06F 40/279* (2020.01); *G16H 20/70* (2018.01)

(58) Field of Classification Search
CPC ........................................................ G06F 40/30
See application file for complete search history.

(56) References Cited

U.S. PATENT DOCUMENTS 11,393,462 B1 7/2022 Gyanchandani et al.
2015/0213002 A1* 7/2015 Gou ........................ G06F 40/30 704/9
(Continued)

FOREIGN PATENT DOCUMENTS

JP 2015090506 A 5/2015
JP 2015099304 A 5/2015
(Continued)

OTHER PUBLICATIONS

Dougherty, Robert F., et al. "Psilocybin Therapy for Treatment Resistant Depression: Prediction of Clinical Outcome by Natural Language Processing." PsyArXiv, published on "Sep. 30, 2022" (Year: 2022).*
(Continued)

*Primary Examiner* — Jialong He
(74) *Attorney, Agent, or Firm* — Hogan Lovells Cadwalader US LLP

(57) ABSTRACT

Approaches for generating predictions related to a set of input text are provided. Text can be received. A machine learning model can be utilized to determine a set of classification probabilities of the text relative to a set of anchor points. A sentiment score indicative of an emotional content of the text can be determined based, at least in part, upon a convex combination of the set of probabilities for the text. One or more predictions related to the text can be generated.

8 Claims, 9 Drawing Sheets

Related U.S. Application Data

(60) Provisional application No. 63/506,447, filed on Jun. 6, 2023, provisional application No. 63/414,769, filed on Oct. 10, 2022, provisional application No. 63/392,451, filed on Jul. 26, 2022.

(51) Int. Cl.

| | |
|---|---|
| ***G06F 40/30*** | (2020.01) |
| ***G10L 25/30*** | (2013.01) |
| ***G16H 20/70*** | (2018.01) |

(56) References Cited

U.S. PATENT DOCUMENTS

| | | | | |
|---|---|---|---|---|
| 2020/0286505 | A1* | 9/2020 | Osborne | G10H 1/00 |
| 2021/0110895 | A1 | 4/2021 | Shriberg et al. | |
| 2022/0027570 | A1* | 1/2022 | Kohli | G06N 3/044 |

FOREIGN PATENT DOCUMENTS

| | | | |
|---|---|---|---|
| JP | 2018156272 | A | 10/2018 |
| JP | 2018195043 | A | 12/2018 |
| JP | 2021510851 | A | 4/2021 |
| JP | 2021529382 | A | 10/2021 |
| JP | 2022106068 | A | 7/2022 |

OTHER PUBLICATIONS

Lee, Lung-Hao, Jian-Hong Li, and Liang-Chih Yu. "Chinese EmoBank: Building valence-arousal resources for dimensional sentiment analysis." Transactions on Asian and Low-Resource Language Information Processing 21.4 (Jan. 2022) (Year: 2022).*

Mehrabian, Albert. "Pleasure-arousal-dominance: A general framework for describing and measuring individual differences in temperament." Current Psychology 14 (1996). (Year: 1996).*

Verma, Gyanendra K., and Uma Shanker Tiwary. "Affect representation and recognition in 3D continuous valence-arousal-dominance space." Multimedia Tools and Applications 76 (2017) (Year: 2017).*

Xie, Housheng, et al. "A multi-dimensional relation model for dimensional sentiment analysis." Information Sciences 579 (2021): 832-844. (Year: 2021).*

International Search Report and Written Opinion issued on Oct. 27, 2023 in PCT Application No. PCT/US2023/070896 (14 total pages).

Anwar et al.", Analyzing Public Opinion Based on Emotion Labeling Using Transformers", 2021 2nd International Conference on Innovative and Creative Information Technology (ICITECH), IEEE, XP034015587, Sep. 23, 2021, pp. 74-78 (5 total pages).

Joshi, "1. BART: Denoising Autoencoder for Pretraining Sequence-to-Sequence Models [Multi-Class Classifier]", Kaggle, Dec. 31, 2020, XP093091903, https://www.kaggle.com/code/akshay560/sentiment-analysis-with-bart-covid19, pp. 1-9 (9 total pages).

Anonymous, "bart-large-mnli", Hugging Face, README.md, facebook/bart-large-mnli at c626438eeca63a93bd6024b0a0f8b3c0c30d7b, XP093091881, Aug. 9, 2021, pp. 1-2 (2 total pages).

Anonymous, "bart-large-mnli", Hugging Face, Commits, facebook/bart-large-mnli, XP093091885, Aug. 9, 2021, p. 1 (1 total page).

Clarke et al., "From a Large Language Model to Three-Dimensional Sentiment", XP093091685, Jul. 28, 2023, doi: 10.31234/osf.io/kaeqy, pp. 1-23 (23 total pages).

International Search Report and Written Opinion re-issued for Dec. 15, 2023 in PCT Application No. PCT/US2023/070857, 14 pages.

Dougherty et al., "Psilocybin therapy for treatment resistant depression: prediction of clinical outcome by natural language processing", XP93092800A, Aug. 22, 2023, Psychopharmacology, https://doi.org/10.1007/sc00213-023-06432-5, 9 pages.

Dougherty et al., "Supplemental Materials for Psilocybin Therapy for Treatment Resistant Depression: Prediction of Clinical Outcome by Natural Language Processing", XP93092805A, Aug. 22, 2023, 13 pages.

Tai et al., "Development and Evaluation of a Therapist Training Program for Psilocybin Therapy for Treatment-Resistant Depression in Clinical Research", Feb. 3, 2021, Frontiers in Psychiatry, vol. 12, XP093091755, doi: 10.3389/fpsyt.2021.586682, 9 pages.

Joshi, "1. BART: Denoising Autoencoder for Pretraining Sequence-to-Sequence Models [Multi-Class Classifier]", Kaggle, Dec. 31, 2020, XP093091903, https://www.kaggle.com/code/akshay560/sentiment-analysis-with-bart-covid19, 9 pages.

Wu et al., "THU_NGN at IJCNLP-2017 Task 2: Dimensional Sentiment Analysis for Chinese Phrases with Deep LSTM", Dec. 1, 2017, https://aclanthology.org/117-4007, 6 pages.

* cited by examiner

200

| | utterance | speaker | valence | arousal | confidence |
|---|---|---|---|---|---|
| 0 | Good morning. | Therapist | 0.563 | -0.115 | 0.073 |
| 1 | Hello, Dr. Rogers. | Patient | 0.470 | 0.038 | -0.062 |
| 2 | I'm Dr. Rogers, you must be Gloria. | Therapist | 0.330 | 0.031 | 0.003 |
| 3 | Yes, I am. | Patient | 0.517 | -0.296 | 0.346 |
| 4 | Won't you have a chair? | Therapist | -0.225 | 0.149 | 0.100 |
| 5 | Now then, we have half an hour together, and I really don't know what we will be able to make of it but uh I hope we can make something of it. | Therapist | 0.175 | -0.005 | -0.157 |
| 6 | I'd be glad to know whatever concerns you. | Therapist | 0.444 | 0.105 | -0.192 |
| 7 | Well, right now I'm nervous, but I feel more comfortable the way you are talking in a low voice and I don't feel like you'll be so harsh on me. | Patient | 0.296 | -0.366 | -0.275 |
| 8 | But, ah. | Patient | 0.377 | 0.064 | -0.319 |
| 9 | I hear the tremor in your voice so I know you are. | Therapist | -0.331 | 0.386 | -0.311 |
| 10 | Uh, well, the main thing I um, want to talk to you about is uh, I'm just newly divorced and uh I had gone in therapy before and I felt comfortable when I left, and all of a sudden now the biggest change is adjusting to my single life. | Patient | 0.167 | 0.245 | -0.231 |
| 11 | And uh one of the things that bothers me the most is especially men, and having men to the house and how it effects the children and–Uh, the biggest thing I want–the thing that keeps coming to mind I want to tell you about is that I have a daughter, nine, who at one time I felt had a lot of emotional problems. | Patient | -0.147 | 0.271 | -0.017 |
| 12 | I wish I could stop shaking. | Patient | -0.374 | 0.385 | -0.332 |
| 13 | And uh, I'm real conscious of things affecting her. | Patient | -0.211 | 0.282 | -0.143 |
| 14 | I don't want her to get upset, I don't want to shock her. | Patient | -0.150 | -0.495 | 0.145 |
| 15 | I want so bad to–for her to accept me. | Patient | 0.273 | 0.401 | -0.241 |
| 16 | And we're open with each other especially about sex. | Patient | 0.902 | -0.729 | 0.132 |
| 17 | And the other day she saw a girl that was single but pregnant and she asked me all about "can girls get pregnant if they are single?" | Patient | 0.300 | 0.390 | -0.248 |
| 18 | And the conversation was fine and I wasn't unat ease at all with her until she asked me if I had ever made love to a man since I left her daddy and I lied to her. | Patient | 0.129 | 0.206 | -0.114 |

FIG. 2A

COMPUTING N-DIMENSIONAL SENTIMENT USING A LARGE LANGUAGE MODEL

CROSS-REFERENCE TO RELATED APPLICATIONS

This application claims priority to and the benefit of PCT Application Serial No. PCT/US23/70896 filed Jul. 25, 2023 titled "COMPUTING N-DIMENSIONAL SENTIMENT USING A LARGE LANGUAGE MODEL," and U.S. Provisional Application Ser. No. 63/506,447 filed Jun. 6, 2023, titled "FROM A LARGE LANGUAGE MODEL TO THREE-DIMENSIONAL SENTIMENT," and U.S. Provisional Application Ser. No. 63/392,451 filed Jul. 26, 2022 titled "PSILOCYBIN THERAPY FOR TREATMENT RESISTANT DEPRESSION," and U.S. Provisional Application Ser. No. 63/414,769 filed Oct. 10, 2022 titled "PSILOCYBIN THERAPY FOR TREATMENT RESISTANT DEPRESSION," and PCT Application Serial No. PCT/US23/070857 filed Jul. 24, 2023, titled "PSILOCYBIN THERAPY FOR TREATMENT RESISTANT DEPRESSION," and U.S. application Ser. No. 18/274,066 filed Jul. 25, 2023, titled "PSILOCYBIN THERAPY FOR TREATMENT RESISTANT DEPRESSION," the full disclosures of which are hereby incorporated herein by reference in their entirety for all purposes.

BACKGROUND

Recent advances in artificial intelligence have provided the building blocks necessary for quantifying the sentiment of human language. One form of human interaction that is important in the mental health context is that between a therapist and patient. Therapeutic administration of psychedelic drugs has shown significant potential, both in historical accounts and in recent clinical trials on the treatment of depression and other related mental and behavioral disorders. For example, recent studies have shown promising results when using psilocybin formulations for patients with treatment-resistant depression (TRD). However, while promising, such a treatment may only work for a portion of the population, and early prediction of an outcome is a key objective for treatment. Having the ability to quantify language spoken during a therapy session, at scale, using natural language processing (NLP) methods in combination with other methods can help bring unprecedented precision and rigor to the analysis of human language.

Psychological descriptions of emotion can generally involve one of two approaches: categorical or dimensional. The categorical approach can sort emptions among a number of discrete categories with distinct boundaries separating emotional states. In contrast, dimensional approaches to emotion attempt to define a continuous space of emotion, within which the traditional categorical emotions can be placed. While simple NLP methods based on a categorical approach to emotion such as positive-negative sentiment classifiers have been available, an NLP model based on a n-dimensional approach to emotion can provide a more complete and nuanced measurement of language.

BRIEF DESCRIPTION OF THE DRAWINGS

Various embodiments in accordance with the present disclosure will be described with reference to the drawings, in which:

FIGS. 2A and 2B illustrate an example therapy session transcript and a time series showing the smoothed average of the valence, arousal, and confidence scores for the therapist and patient for the session, respectively.

DETAILED DESCRIPTION

A three-dimensional valence-arousal-confidence (VAC) framework can be used to describe a wide variety of emotional states that represent the full range of human responses, and also captures essential features of categorical emotions. In accordance with various embodiments, a VAC model can be used to express the sentiment of given input text as a convex combination whose weights are obtained from class scores of a zero-shot classifier built from a large language model (LLM). Approaches using the VAC model can contribute to more accurate sentiment differences being captured between sentences that are missed or misinterpreted by previous approaches using only the categorical approach or lower dimensional models.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Major depressive disorder (MDD) is a debilitating disease and can affect one in six adults in their lifetime. MDD may be characterized by at least one depressive episode having a duration of at least two weeks and involving clear changes in mood, cognition, and the ability to experience pleasure. While MDD may be effectively managed using psychotherapy and/or pharmacological treatments, some MDD patients may not respond to treatment, despite multiple treatment attempts. Such individuals may be referred to as patients having treatment-resistant depression (TRD). There are various existing options for treatment, but they are often determined to be unsatisfactory. Therefore, there is a need for the development of alternative therapeutic options for TRD patients that have improved efficacy. Additionally, acceptability of a condition or treatment may remain an important challenge for such patients.

Psilocybin is a tryptamine alkaloid whose potential as an effective antidepressant was preliminarily studied in patients with life-threatening cancer, MDD, and TRD. In at least one psilocybin study using a 25 mg dose of COMP360, a set of participants experienced reduced depression symptoms for as many as 12 weeks. While very promising, these results show that a durable psilocybin response occurs in only a portion of the TRD population. Weeks may pass while potential opportunities for additional treatment are potentially wasted. While this example describes the application of the model in the therapeutic space, the model can be used for any other applications related to the quantification of language or in applications where there is a need to understand the sentiment of such language.

Figure 1:
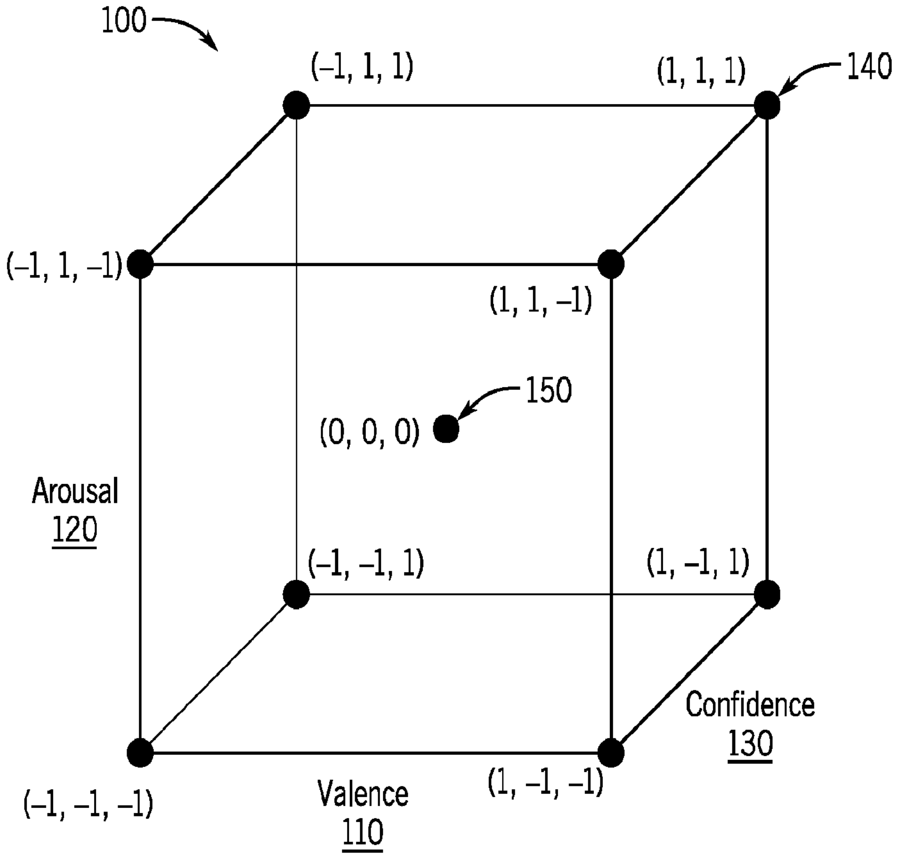
FIG. 1 illustrates an example diagram of anchor points that can be utilized in accordance with various embodiments.

FIG. 1 illustrates an example three-dimensional sentiment cube 100 that can be utilized in accordance with various embodiments. In at least some embodiments, a model may utilize a weighted average of nine "anchor" points in a three-dimensional cube to produce values along three sentiment dimensions: valence 110, arousal 120, and confidence 130. In the case of n dimensions, where n is any positive integer, there are $2^n$ anchor points within an n-cube at the vertices as well as additional anchor points, such as the one at the center of the n-cube. "Confidence" in accordance with one or more embodiments can be defined as the degree to which a piece of text communicates the emotional state of confidence and assuredness, as opposed to a confidence metric provided by a machine learning classifier. The weights for the weighted average may be computed from numbers produced by a classifier for a set of classes corresponding to the various dimensions. Such an approach may help predict whether a participant will respond at a particular week in their treatment timeline. The architecture can be built from a geometrical operation called a convex combination. In accordance with this example, nine points 140 of the cube 100 can be considered, centered at the origin: the eight corners (±1, ±1, ±1) and the center 150 at (0, 0, 0). While this example describes three dimensions, an n-dimensional model can be used for any number of sentiment dimensions. The ability to quantify language in this way, above a two-dimensional model, can make it such that results are more accurate than what a human therapist would come up with. Further, different humans will likely have differing opinions on what a piece of text means, so using approaches such as those described herein can help ensure objective results that are more accurate holistically.

In accordance with an example embodiment, audio recordings of a therapy session may be collected and transcribed into dialogue text through the use of natural language processing (NLP) techniques. The transcripts may then be parsed into individual "utterances" used to estimate session sentiment for the therapist and the patient or participant using a sentiment model. Such a model may produce valence, arousal, and confidence scores for each utterance.

In at least some embodiments, audio may be parsed and tagged to the utterances. The audio may be processed using a model to predict a patient's tone. In some embodiments, the audio may be correlated with a score indicative of a patient's tone. The audio score may be compared to the valence and arousal scores, or the audio score may be accounted for with the valence and arousal scores. A zero-shot classifier built on a Bidirectional AutoRegressive Transformer (BART) autoencoder and Multi-Genre Natural Language Inference (MNLI) dataset may be used to calculate the sentiment valence, arousal, and confidence scores.

For given text u and an anchor point p, for each point a number $w_p(u)$ (called the weight of u at p) can be defined. These numbers can satisfy the following properties:

$$w_p(u) \geq 0, \text{ and}$$

$$\sum_p w_p(u) = 1,$$

where the sum is over all anchor points p.

With these weights, the three-dimensional VAC sentiment can be expressed as:

$$(\text{valence}(u), \text{ arousal } (u), \text{ confidence } (u)) = \sum_p w_p(u)p.$$

This can also be expressed as:

$$\text{valence}(u) = \sum_p w_p(u)p_1$$

$$\text{arousal}(u) = \sum_p w_p(u)p_2$$

$$\text{confidence}(u) = \sum_p w_p(u)p_3$$

where $p=(p_1, p_2, p_3)$. The properties of the weights can guarantee the sentiment values lie between −1 and 1.

In accordance with an example embodiment, the quote "Heal yourself, with beautiful love, and always remember . . . you are the medicine" can have the following anchor weight values for the quote:

$$w_{(1,1,1)} = 0.204866$$

$$w_{(1,1,-1)} = 0.223669$$

$$w_{(1,-1,1)} = 0.249116$$

$$w_{(1,-1,-1)} = 0.130423$$

$$w_{(-1,1,1)} = 0.023099$$

$$w_{(-1,1,-1)} = 0.012893$$

$$w_{(-1,-1,1)} = 0.103748$$

$$w_{(-1,-1,-1)} = 0.011839$$

$$w_{(0,0,0)} = 0.040327$$

In this case, the sentiment score can be calculated as:

$$\text{valence}(u) = 0.204886*1 + 0.249116*1 + 0.130423*1 + 0.023099*(-1) + 0.012893*(-1) + 0.103748*(-1) + 0.011839*(-1) + 0.040327*0 = 0.684102.$$

Using the same approach, arousal (u)=−0.032 and confidence (u)=0.211. All together:

$$(\text{valence}(u), \text{arousal}(u), \text{confidence}(u)) = (0.684102, -0.031864, 0.210515)$$

The weights can change depending on the number of anchor points, the number of dimensions, and the type of input being processed. In accordance with an example embodiment, anchor weights $w_p(u)$ for a string of text u and an anchor point p are computed using a zero-shot classifier built using the BART autoencoder that has been fine-tuned on the Multi-Genre Natural Language Inference (MNLI) dataset. Predictions given by the classifier can be combined to produce weights used in the model. The choice of classes themselves is a difficult to tune hyperparameter. The classes can be used to arrive at these classes and group them into "anchor lists."

In accordance with an example embodiment, input text can be passed to the BART-MNLI classifier including, but not limited to, the following classes: accepting, adequate, aggressive, astonishing, awed, comfortable, confident, controlling, dazzled, defiant, destructive, detached, discouraged, eager, enraged, exhilarated, feeble, frustration, humiliation, inferior, joy, loneliness, neutral, nothingness, panicked, permissiveness, powerful, relaxed, resistant, secure, serious, sheltered, soft, stoic, suffering, surprised, terrified, tolerant, tranquil, triumphant, victorious, and wise. Any number of classes may be chosen, including more or fewer than the classes described herein.

For text u, the values $P_c(u)$=the probability that u is in class c. This probability can be computed under the assumption that c is in one of the classes and that the classes are mutually exclusive. Classes, in accordance with an example embodiment, can be separated into lists, with one list for each of the nine anchor points, p, using frequency-inverse document frequency techniques:

a weight that includes the "joy" class score as a summand. In short, classes in the (1,1,1)-class list should be (1,1,1) words (or close to it). The same goes for other anchors.

Class lists can be compiled by collecting sentences spoken in therapy sessions and scoring those sentences. Once score, large numbers of sentences for each affective state corresponding to the anchor points can be collected, and words which are most characteristic of each document can be extracted.

Sentiment scores of an utterance can depend on weights $w_p(u)$ and these weights can depend on probabilities $P_c(u)$. For a piece of text u, the number $P_c(u)$ can depend not only on c but on the whole set of classes. If different classes were to be used in the anchor lists, the numbers $P_c(u)$ change, even for classes c which are not changed. At a surface level, it would appear that all the numbers $P_c(u)$ would have to be recomputed from scratch, but using the BART-MNLI zero-shot classifier can greatly accelerate computing $P_c(u)$ regardless of other classes involved.

Internal to the BART-MNLI zero-shot classifier a number Lc(u) is calculated that is independent of the other classes. This number may be referred to as the log-odds of the entailment probability, also known as a "logit." The entailment probability is a prediction that the text u is a member of the class c without any information about the other classes. Computing entailment probabilities is the task that BART-MNLI is tuned to upstream of its zero-shot application. Logits for all classes c that are planned for exploration and all words and utterances u that will be used in evaluating a model can be pre-computed. In this way, it is possible to $$(1, 1, 1) - \text{classes} = [\text{exhilarated, joy, triumphant, victorious, powerful}]$$

$$(1, 1, -1) - \text{classes} = [\text{astonishing, awed, dazzled, eager, surprised}]$$

$$(1, -1, 1) - \text{classes} = [\text{comfortable, confident, relaxed, secure, wise}]$$

$$(1, -1, -1) - \text{classes} = [\text{accepting, sheltered, soft, tranquil, tolerant}]$$

$$(-1, 1, 1) - \text{classes} = [\text{aggressive, controlling, defiant, destructive, enraged}]$$

$$(-1, 1, -1) - \text{classes} = [\text{frustration, humiliation, panicked, suffering, terrified}]$$

$$(-1, -1, 1) - \text{classes} = [\text{adequate, detached, resistant, serious, stoic}]$$

$$(-1, -1, -1) - \text{classes} = [\text{discouraged, feeble, inferior, loneliness, nothingness}]$$

$$(0, 0, 0) - \text{classes} = [\text{neutral, permissiveness}]$$

The weights $w_p(u)$ are computed as:

$$w_p(u) = \sum_{c \in p-classes} P_c(u)$$

The choice of the classes and how they are separated into anchor lists contribute to how the model scores a piece of text. The basic behavior that guides the intuition behind what classes should appear in an anchor list is that the more highly a piece of text scores for the classes in a given anchor list, the greater the anchor weight will be, and consequently the more strongly the text will be pulled toward the anchor. Thus, the classes that appear in the list of a given anchor should reflect the sentiment the anchor represents.

For example, if "joy" is in the anchor list for the anchor (1,1,1), and a piece of text scores highly for the class "joy," then the model will pull the text toward the point (1,1,1) with test as many choices as possible of classes or different assignments of classes to anchor class lists in a computationally efficient manner.

Figure 2B:
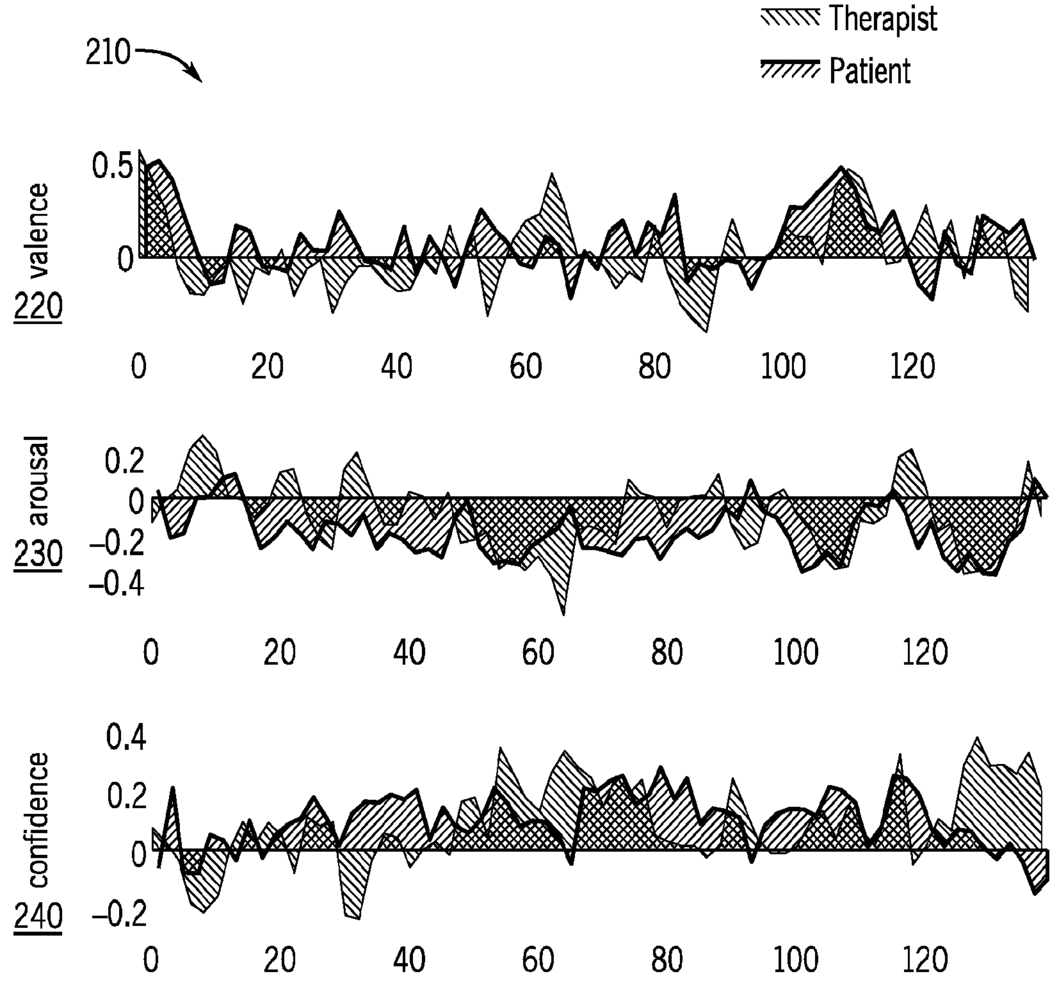
Figure 2C:
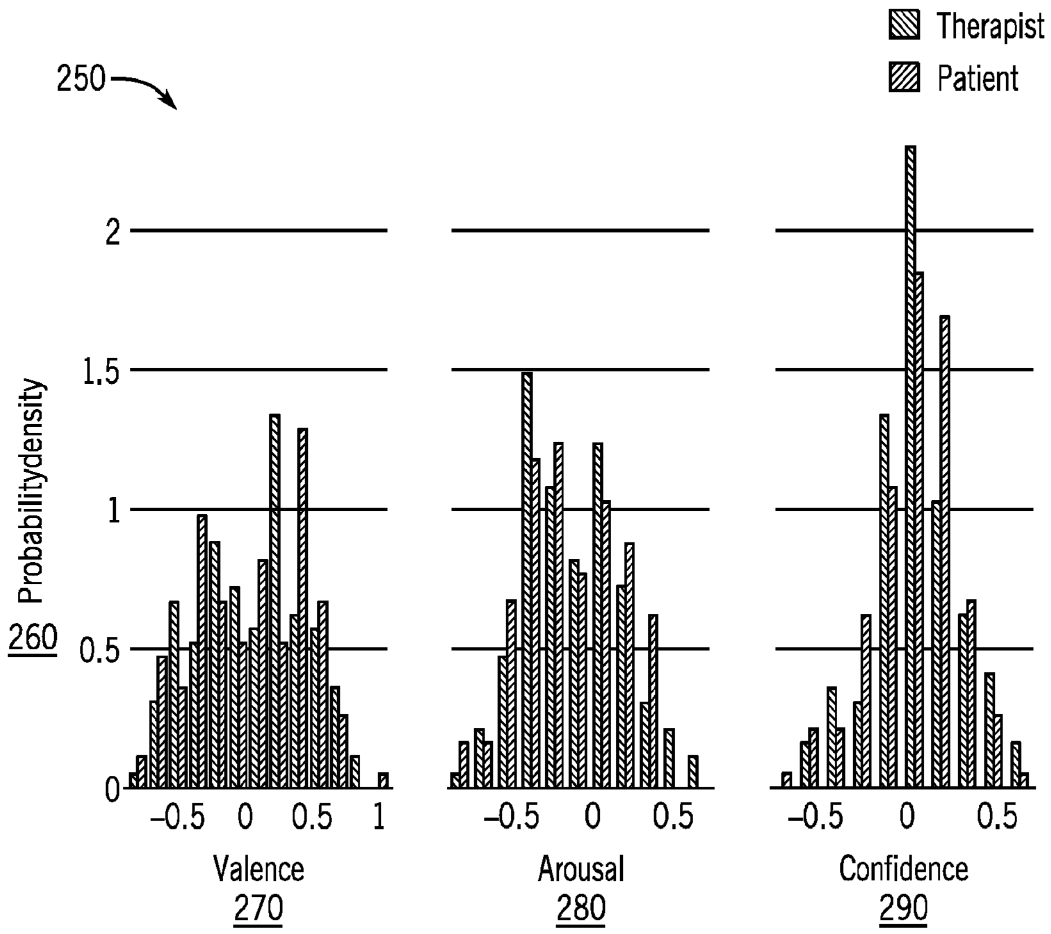
FIG. 2C illustrates an example distribution for a patient and therapist that can be utilized in accordance with various embodiments.

FIGS. 2A and 2B illustrate an example therapy session transcript 200 and a time series 210 showing the smoothed average of the valence, arousal, and confidence scores (220, 230, 240) for the therapist and patient for the session, respectively. FIG. 2C illustrates an example distribution 250 for a patient and therapist that can be utilized in accordance with various embodiments.

In the example therapy session 200, Gloria, a 30-year-old divorced mother of three, discusses her feelings of anxiety and dissatisfaction with her life. Gloria guides the conversation and expresses her feelings in her own words. According to the VAC model, the session's average sentiment is medium-high valence, neutral arousal, and low confidence for both the therapist and the patient. FIG. 2C illustrates an overall distribution 250 of the valence, arousal, and confidence score (270, 280, 290) for the patient and therapist in the example therapy session 200, graphically provided as a probability density 240.

Figure 3:
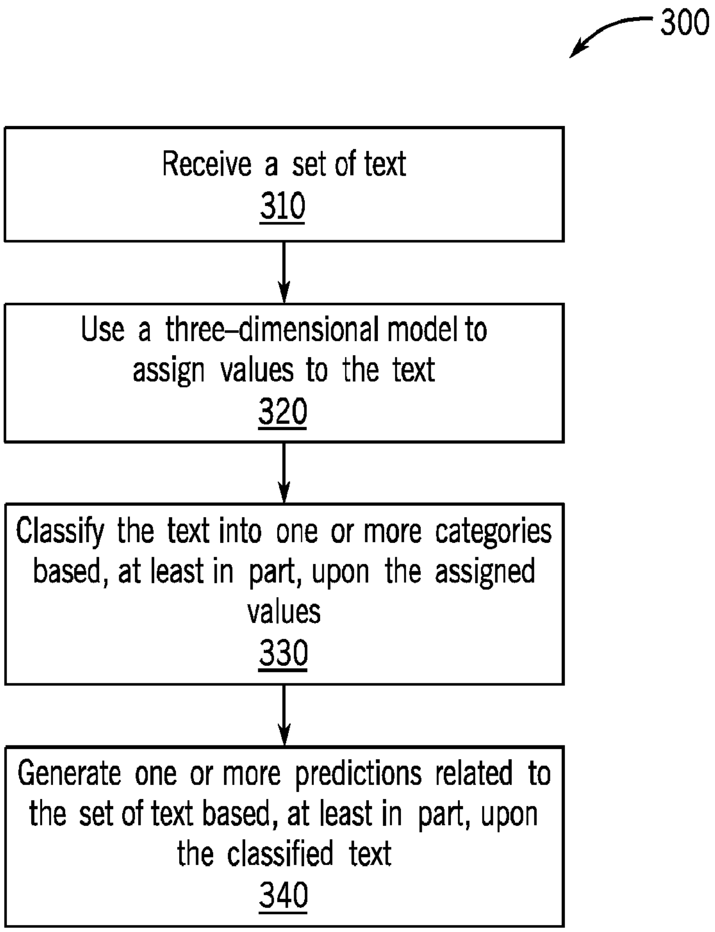
FIG. 3 illustrates an example method that can be utilized to implement one or more aspects of the various embodiments.

FIG. 3 illustrates an example method 300 that can be utilized to implement one or more aspects of the various embodiments. In accordance with an example embodiment, text can be received 310. For example, an audio recording may be generated at the time of an initial integration session between patient or participant and the medical provider, such as a therapist. Using one or more NLP techniques, the recording may be transcribed to text.

A trained large language model may be utilized, in accordance with one or more embodiments, to help score utterances. For example, a machine learning model may analyze the text and determine a set of classification probabilities of the text relative to a set of anchor points 320.

Text may be scored or valued in three or more dimensions, including, but not limited to, valence, arousal, and confidence. In this way, sentiment may capture intensity, rather than just positivity or negativity. The sentiment score of a piece of text may be distinguishable from trying to infer an emotional state of a speaker. For example, text reciting "I love broccoli" may be scored by traditional sentiment models as being positive. However, if vocalized in a sarcastic way, the text would signal a negative attitude towards broccoli.

A sentiment score indicative of an emotional content of the text can be determined based, at least in part, upon a convex combination of the set of probabilities for the text 330. In some example embodiments, a classifier may be utilized to classify the text. Such a classifier may be built on a BART autoencoder and Multi-Genre Natural Language Inference (MNLI) dataset. The use of a model built on top of larger models may enable the use of almost unlimited freely available data for smaller data tasks.

One or more predictions related to the text can be generated 340. For example, a prediction may correspond to a predicted response to an administered therapy, or any other type of prediction related to the set of text. It should be understood that for any process herein there can be additional, fewer, or alternative steps performed in similar or alternative orders, or in parallel, within the scope of the various embodiments unless otherwise specifically stated.

Figure 4:
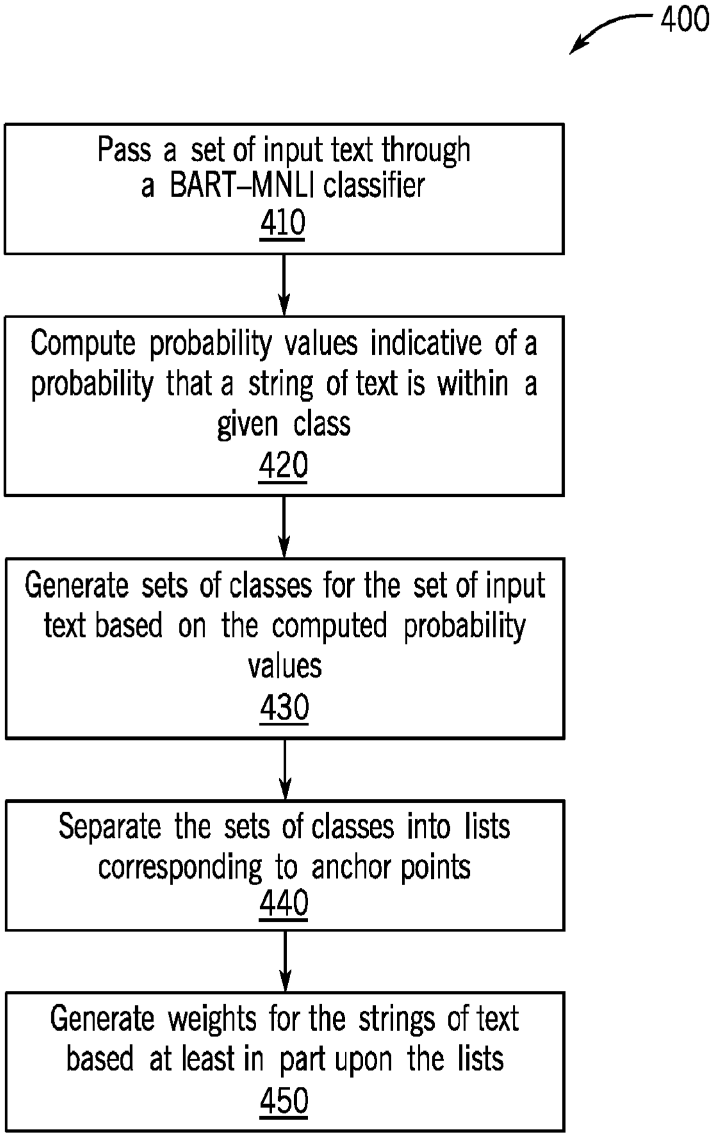
FIG. 4 illustrates an example method that can be utilized to implement one or more aspects of the various embodiments.

FIG. 4 illustrates an example method 400 that can be utilized to implement one or more aspects of the various embodiments. In accordance with an example embodiment, a set of input text can be passed through a BART-MNLI classifier 410. Probability values indicative of a probability that a string of text, of the set of input text, is within a given class can be computed 420. Sets of classes for the set of input text can be generated based on the computed probability values 430. The sets of classes can be separated into lists corresponding to one or more anchor points 440. Weights for the strings of text can be generated based, at least in part, upon the lists 450.

As explained, input text can be passed to the BART-MNLI classifier including, but not limited to, the following classes: accepting, adequate, aggressive, astonishing, awed, comfortable, confident, controlling, dazzled, defiant, destructive, detached, discouraged, eager, enraged, exhilarated, feeble, frustration, humiliation, inferior, joy, loneliness, neutral, nothingness, panicked, permissiveness, powerful, relaxed, resistant, secure, serious, sheltered, soft, stoic, suffering, surprised, terrified, tolerant, tranquil, triumphant, victorious, and wise. Classes, in accordance with an example embodiment, can be separated into lists, with one list for each of the nine anchor points, p:

(1, 1, 1) – classes = [exhilarated, joy, triumphant, victorious, powerful]

(1, 1, −1) – classes = [astonishing, awed, dazzled, eager, surprised]

(1, −1, 1) – classes = [comfortable, confident, relaxed, secure, wise]

(1, −1, −1) – classes = [accepting, sheltered, soft, tranquil, tolerant]

(−1, 1, 1) – classes = [aggressive, controlling, defiant, destructive, enraged]

(−1, 1, −1) – classes = [frustration, humiliation, panicked, suffering, terrified]

(−1, −1, 1) – classes = [adequate, detached, resistant, serious, stoic]

(−1, −1, −1) – classes = [discouraged, feeble, inferior, loneliness, nothingness]

(0, 0, 0) – classes = [neutral, permissiveness]

Any number of classes may be chosen, including more or fewer than the classes described herein.

Figure 5:
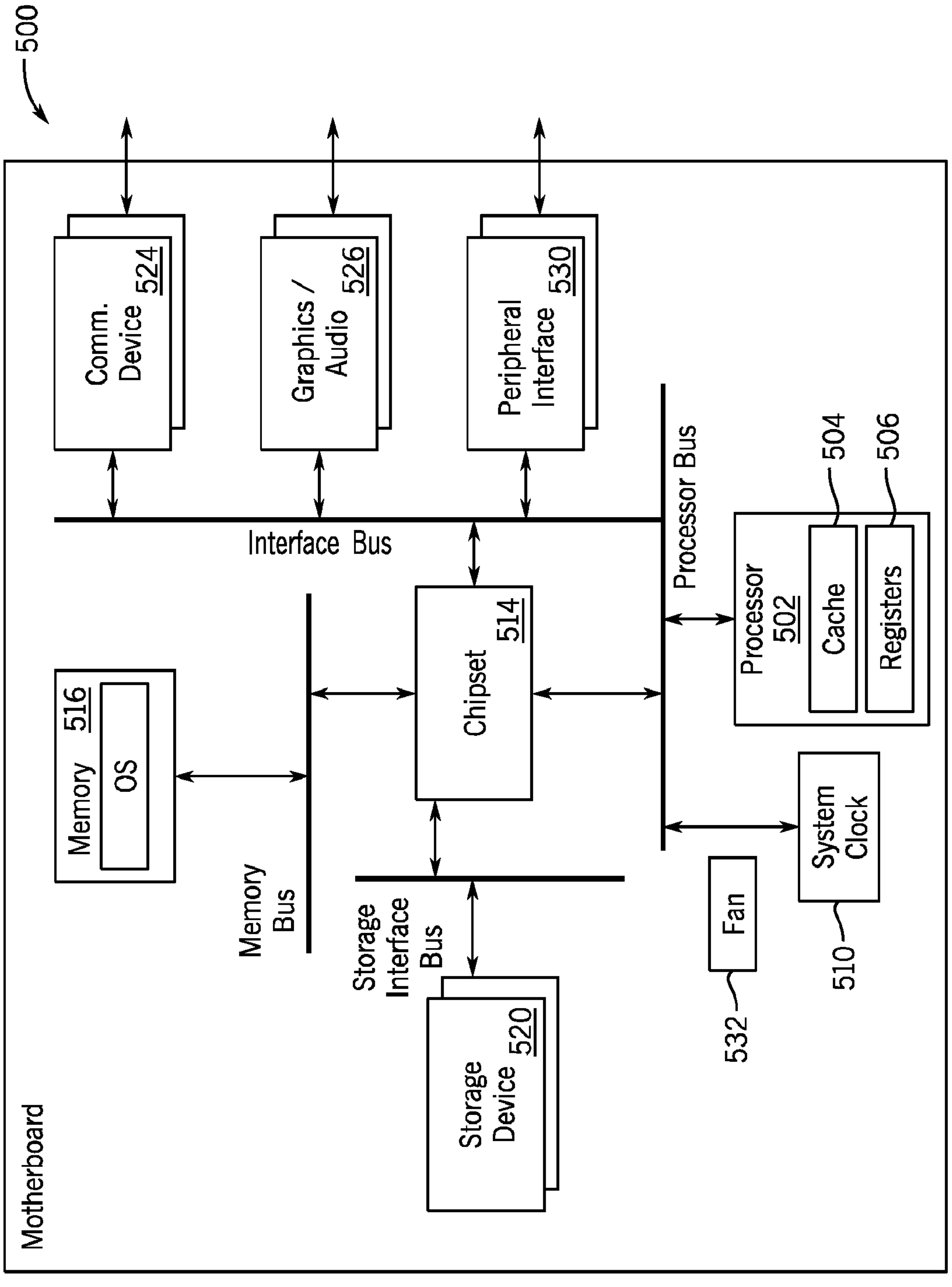
FIG. 5 illustrates components of an example computing device that can be utilized in accordance with various embodiments.

Computing resources, such as servers, that can have software and/or firmware updated in such a matter will generally include at least a set of standard components configured for general purpose operation, although various proprietary components and configurations can be used as well within the scope of the various embodiments. FIG. 5 illustrates components of an example computing device 500 that can be utilized in accordance with various embodiments. As known for computing devices, the computer will have one or more processors 502, such as central processing units (CPUs), graphics processing units (GPUs), and the like, that are electronically and/or communicatively coupled with various components using various buses, traces, and other such mechanisms. A processor 502 can include memory registers 506 and cache memory 504 for holding instructions, data, and the like. In this example, a chipset 514, which can include a northbridge and southbridge in some embodiments, can work with the various system buses to connect the processor 502 to components such as system memory 516, in the form or physical RAM or ROM, which can include the code for the operating system as well as various other instructions and data utilized for operation of the computing device. The computing device can also contain, or communicate with, one or more storage devices 520, such as hard drives, flash drives, optical storage, and the like, for persisting data and instructions similar, or in addition to, those stored in the processor and memory. The processor 502 can also communicate with various other components via the chipset 514 and an interface bus (or graphics bus, etc.), where those components can include communications devices 524 such as cellular modems or network cards, media components 526, such as graphics cards and audio components, and peripheral interfaces 530 for connecting peripheral devices, such as printers, keyboards, and the like. At least one cooling fan 532 or other such temperature regulating or reduction component can also be included as well, which can be driven by the processor or triggered by various other sensors or components on, or remote from, the device. Various other or alternative components and configurations can be utilized as well as known in the art for computing devices.

At least one processor 502 can obtain data from physical memory 516, such as a dynamic random-access memory (DRAM) module, via a coherency fabric in some embodiments. It should be understood that various architectures can be utilized for such a computing device, that may include varying selections, numbers, and arguments of buses and bridges within the scope of the various embodiments. The data in memory may be managed and accessed by a memory controller, such as a DDR controller, through the coherency fabric. The data may be temporarily stored in a processor cache 504 in at least some embodiments. The computing device 500 can also support multiple I/O devices using a set of I/O controllers connected via an I/O bus. There may be I/O controllers to support respective types of I/O devices, such as a universal serial bus (USB) device, data storage (e.g., flash or disk storage), a network card, a peripheral component interconnect express (PCIe) card or interface 530, a communication device 524, a graphics or audio card 526, and a direct memory access (DMA) card, among other such options. In some embodiments, components such as the processor, controllers, and caches can be configured on a single card, board, or chip (i.e., a system-on-chip implementation), while in other embodiments at least some of the components may be located in different locations, etc.

An operating system (OS) running on the processor 502 can help to manage the various devices that may be utilized to provide input to be processed. This can include, for example, utilizing relevant device drivers to enable interaction with various I/O devices, where those devices may relate to data storage, device communications, user interfaces, and the like. The various I/O devices will typically connect via various device ports and communicate with the processor and other device components over one or more buses. There can be specific types of buses that provide for communications according to specific protocols, as may include peripheral component interconnect) PCI or small computer system interface (SCSI) communications, among other such options. Communications can occur using registers associated with the respective ports, including registers such as data-in and data-out registers. Communications can also occur using memory mapped I/O, where a portion of the address space of a processor is mapped to a specific device, and data is written directly to, and from, that portion of the address space.

Such a device may be used, for example, as a server in a server farm or data warehouse. Server computers often have a need to perform tasks outside the environment of the CPU and main memory (i.e., RAM). For example, the server may need to communicate with external entities (e.g., other servers) or process data using an external processor (e.g., a General Purpose Graphical Processing Unit (GPGPU)). In such cases, the CPU may interface with one or more I/O devices. In some cases, these I/O devices may be special-purpose hardware designed to perform a specific role. For example, an Ethernet network interface controller (NIC) may be implemented as an application specific integrated circuit (ASIC) comprising digital logic operable to send and receive packets.

In an illustrative embodiment, a host computing device is associated with various hardware components, software components and respective configurations that facilitate the execution of I/O requests. One such component is an I/O adapter that inputs and/or outputs data along a communication channel. In one aspect, the I/O adapter device can communicate as a standard bridge component for facilitating access between various physical and emulated components and a communication channel. In another aspect, the I/O adapter device can include embedded microprocessors to allow the I/O adapter device to execute computer executable instructions related to the implementation of management functions or the management of one or more such management functions, or to execute other computer executable instructions related to the implementation of the I/O adapter device. In some embodiments, the I/O adapter device may be implemented using multiple discrete hardware elements, such as multiple cards or other devices. A management controller can be configured in such a way to be electrically isolated from any other component in the host device other than the I/O adapter device. In some embodiments, the I/O adapter device is attached externally to the host device. In some embodiments, the I/O adapter device is internally integrated into the host device. Also in communication with the I/O adapter device may be an external communication port component for establishing communication channels between the host device and one or more network-based services or other network-attached or direct-attached computing devices. Illustratively, the external communication port component can correspond to a network switch, sometimes known as a Top of Rack ("TOR") switch. The I/O adapter device can utilize the external communication port component to maintain communication channels between one or more services and the host device, such as health check services, financial services, and the like.

The I/O adapter device can also be in communication with a Basic Input/Output System (BIOS) component. The BIOS component can include non-transitory executable code, often referred to as firmware, which can be executed by one or more processors and used to cause components of the host device to initialize and identify system devices such as the video display card, keyboard and mouse, hard disk drive, optical disc drive and other hardware. The BIOS component can also include or locate boot loader software that will be utilized to boot the host device. For example, in one embodiment, the BIOS component can include executable code that, when executed by a processor, causes the host device to attempt to locate Preboot Execution Environment (PXE) boot software. Additionally, the BIOS component can include or takes the benefit of a hardware latch that is electrically controlled by the I/O adapter device. The hardware latch can restrict access to one or more aspects of the BIOS component, such controlling modifications or configurations of the executable code maintained in the BIOS component. The BIOS component can be connected to (or in communication with) a number of additional computing device resources components, such as processors, memory, and the like. In one embodiment, such computing device resource components may be physical computing device resources in communication with other components via the communication channel. The communication channel can correspond to one or more communication buses, such as a shared bus (e.g., a processor bus, a memory bus), a point-to-point bus such as a PCI or PCI Express bus, etc., in which the components of the bare metal host device communicate. Other types of communication channels, communication media, communication buses or communication protocols (e.g., the Ethernet communication protocol) may also be utilized. Additionally, in other embodiments, one or more of the computing device resource components may be virtualized hardware components emulated by the host device. In such embodiments, the I/O adapter device can implement a management process in which a host device is configured with physical or emulated hardware components based on a variety of criteria. The computing device resource components may be in communication with the I/O adapter device via the communication channel. In addition, a communication channel may connect a PCI Express device to a CPU via a northbridge or host bridge, among other such options.

In communication with the I/O adapter device via the communication channel may be one or more controller components for managing hard drives or other forms of memory. An example of a controller component can be a SATA hard drive controller. Similar to the BIOS component, the controller components can include or take the benefit of a hardware latch that is electrically controlled by the I/O adapter device. The hardware latch can restrict access to one or more aspects of the controller component. Illustratively, the hardware latches may be controlled together or independently. For example, the I/O adapter device may selectively close a hardware latch for one or more components based on a trust level associated with a particular user. In another example, the I/O adapter device may selectively close a hardware latch for one or more components based on a trust level associated with an author or distributor of the executable code to be executed by the I/O adapter device. In a further example, the I/O adapter device may selectively close a hardware latch for one or more components based on a trust level associated with the component itself. The host device can also include additional components that are in communication with one or more of the illustrative components associated with the host device. Such components can include devices, such as one or more controllers in combination with one or more peripheral devices, such as hard disks or other storage devices. Additionally, the additional components of the host device can include another set of peripheral devices, such as Graphics Processing Units ("GPUs"). The peripheral devices and can also be associated with hardware latches for restricting access to one or more aspects of the component. As mentioned above, in one embodiment, the hardware latches may be controlled together or independently.

Figure 6:
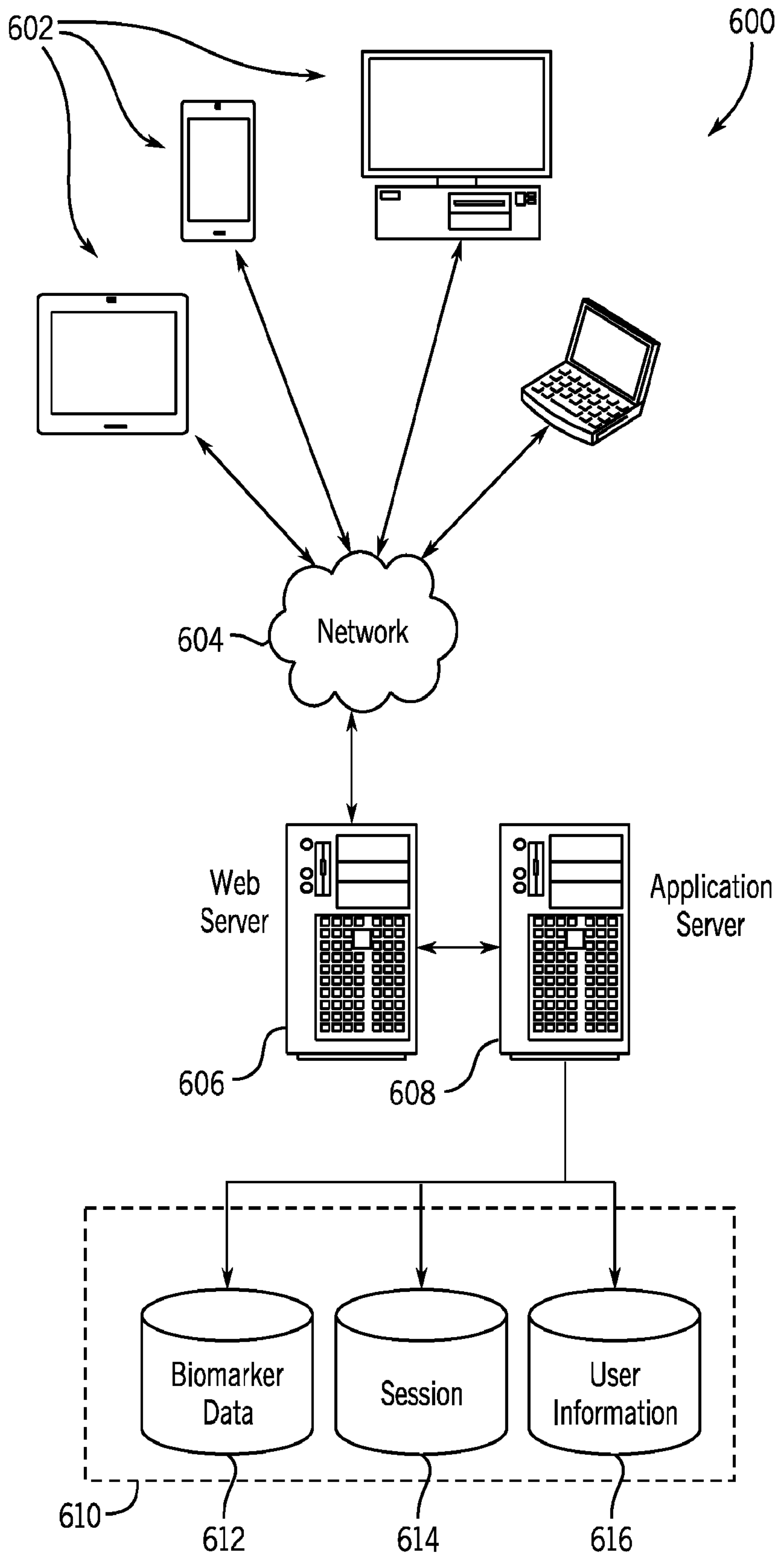
FIG. 6 illustrates an example of an environment for implementing aspects in accordance with various embodiments.

As discussed, different approaches can be implemented in various environments in accordance with the described embodiments. For example, FIG. 6 illustrates an example of an environment 600 for implementing aspects in accordance with various embodiments. As will be appreciated, although a Web-based environment is used for purposes of explanation, different environments may be used, as appropriate, to implement various embodiments. The system includes an electronic client device 602, which can include any appropriate device operable to send and receive requests, messages or information over an appropriate network 604 and convey information back to a user of the device. Examples of such client devices include personal computers, cell phones, handheld messaging devices, laptop computers, set-top boxes, personal data assistants, electronic book readers and the like. Examples of such recipients or users may include medical providers including therapists, or patients. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server 606 for receiving requests and serving content in response thereto, although for other networks, an alternative device serving a similar purpose could be used, as would be apparent to one of ordinary skill in the art.

The illustrative environment includes at least one application server 608 and a data store 610. It should be understood that there can be several application servers, layers or other elements, processes or components, which may be chained or otherwise configured, which can interact to perform tasks such as obtaining data from an appropriate data store. As used herein, the term "data store" refers to any device or combination of devices capable of storing, accessing and retrieving data, which may include any combination and number of data servers, databases, data storage devices and data storage media, in any standard, distributed or clustered environment. The application server 608 can include any appropriate hardware and software for integrating with the data store 610 as needed to execute aspects of one or more applications for the client device and handling a majority of the data access and business logic for an application. The application server provides access control services in cooperation with the data store and is able to generate content such as text, graphics, audio and/or video to be transferred to the user, which may be served to the user by the Web server 606 in the form of HTML, XML or another appropriate structured language in this example. The handling of all requests and responses, as well as the delivery of content between the client device 602 and the application server 608, can be handled by the Web server 606. It should be understood that the Web and application servers are not required and are merely example components, as structured code discussed herein can be executed on any appropriate device or host machine as discussed elsewhere herein.

The data store 610 can include several separate data tables, databases or other data storage mechanisms and media for storing data relating to a particular aspect. For example, the data store illustrated includes mechanisms for storing biomarker data (e.g., production data) 612 and user information 616, which can be used to serve content for the production side. The data store is also shown to include a mechanism for storing log or session data 614. It should be understood that there can be many other aspects that may need to be stored in the data store, such as page image information and access rights information, which can be stored in any of the above listed mechanisms as appropriate or in additional mechanisms in the data store 610. The data store 610 is operable, through logic associated therewith, to receive instructions from the application server 608 and obtain, update or otherwise process data in response thereto. In one example, a user might submit a search request for a certain type of item. In this case, the data store might access the user information to verify the identity of the user and can access the catalog detail information to obtain information about items of that type. The information can then be returned to the user, such as through a patient or therapist portal including biomarker and diagnosis data accessible through a Web page that the user is able to view via a browser on the user device 602. Information for a particular item of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 6. Thus, the depiction of the system 600 in FIG. 6 should be taken as being illustrative in nature and not limiting to the scope of the disclosure.

Figure 7:
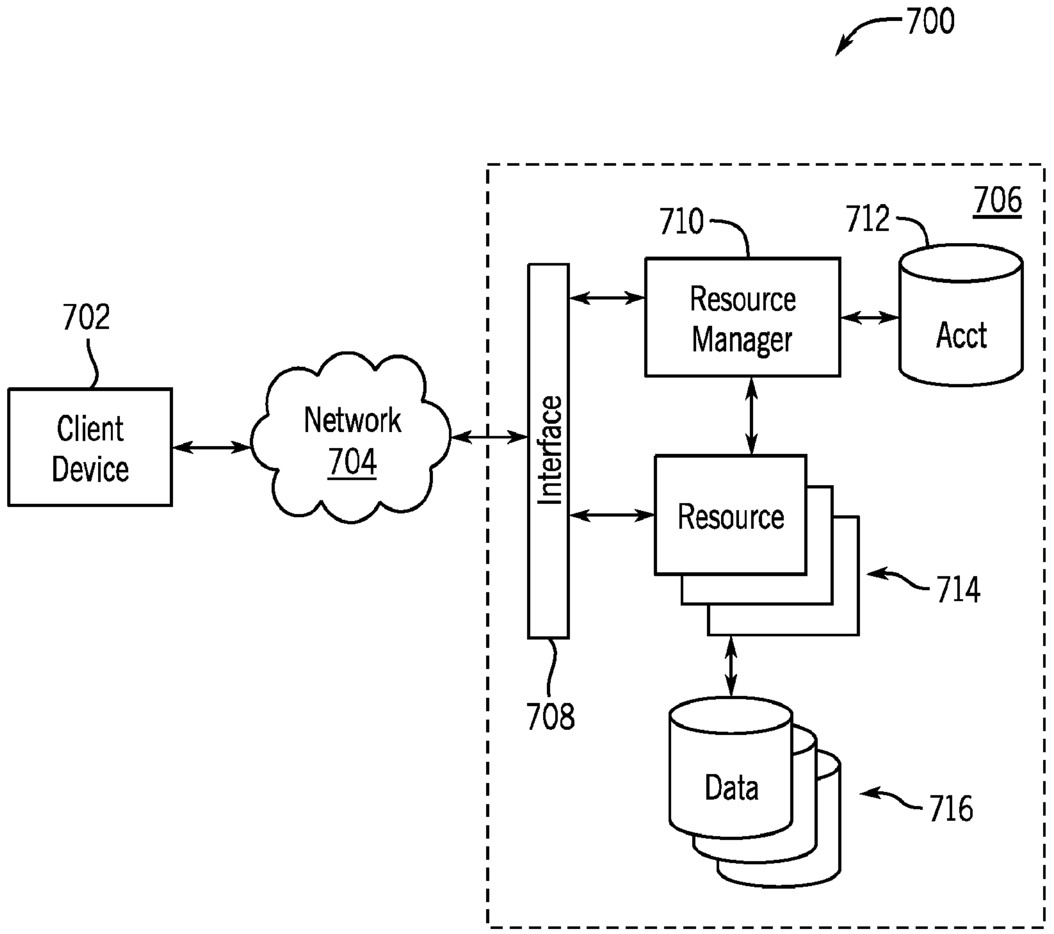
FIG. 7 illustrates components of another example environment in which aspects of various embodiments can be implemented.

FIG. 7 illustrates an example environment 700 in which aspects of the various embodiments can be implemented. In this example a user is able to utilize a client device 702 to submit requests across at least one network 704 to a multi-tenant resource provider environment 706. The client device can include any appropriate electronic device operable to send and receive requests, messages, or other such information over an appropriate network and convey information back to a user of the device. Examples of such client devices include personal computers, tablet computers, smart phones, notebook computers, and the like. The at least one network 704 can include any appropriate network, including an intranet, the Internet, a cellular network, a local area network (LAN), or any other such network or combination, and communication over the network can be enabled via wired and/or wireless connections. The resource provider environment 706 can include any appropriate components for receiving requests and returning information or performing actions in response to those requests. As an example, the provider environment might include Web servers and/or application servers for receiving and processing requests, then returning data, Web pages, video, audio, or other such content or information in response to the request.

In various embodiments, the provider environment may include various types of resources that can be utilized by multiple users for a variety of different purposes. As used herein, computing and other electronic resources utilized in a network environment can be referred to as "network resources." These can include, for example, servers, databases, load balancers, routers, and the like, which can perform tasks such as to receive, transmit, and/or process data and/or executable instructions. In at least some embodiments, all or a portion of a given resource or set of resources might be allocated to a particular user or allocated for a particular task, for at least a determined period of time. The sharing of these multi-tenant resources from a provider environment is often referred to as resource sharing, Web services, or "cloud computing," among other such terms and depending upon the specific environment and/or implementation. In this example the provider environment includes a plurality of resources 714 of one or more types. These types can include, for example, application servers operable to process instructions provided by a user or database servers operable to process data stored in one or more data stores 716 in response to a user request. As known for such purposes, the user can also reserve at least a portion of the data storage in a given data store. Methods for enabling a user to reserve various resources and resource instances are well known in the art, such that detailed description of the entire process, and explanation of all possible components, will not be discussed in detail herein.

In at least some embodiments, a user wanting to utilize a portion of the resources 714 can submit a request that is received to an interface layer 708 of the provider environment 706. The interface layer can include application programming interfaces (APIs) or other exposed interfaces enabling a user to submit requests to the provider environment. The interface layer 808 in this example can also include other components as well, such as at least one Web server, routing components, load balancers, and the like. When a request to provision a resource is received to the interface layer 708, information for the request can be directed to a service manager 710 or other such system, service, or component configured to manage user accounts and information, resource provisioning and usage, and other such aspects. A service manager 710 receiving the request can perform tasks such as to authenticate an identity of the user submitting the request, as well as to determine whether that user has an existing account with the resource provider, where the account data may be stored in at least one account data store 712 in the provider environment. A user can provide any of various types of credentials in order to authenticate an identity of the user to the provider. These credentials can include, for example, a username and password pair, biometric data, a digital signature, or other such information. The provider can validate this information against information stored for the user. If the user has an account with the appropriate permissions, status, etc., the resource manager can determine whether there are adequate resources available to suit the user's request, and if so can provision the resources or otherwise grant access to the corresponding portion of those resources for use by the user for an amount specified by the request. This amount can include, for example, capacity to process a single request or perform a single task, a specified period of time, or a recurring/renewable period, among other such values. If the user does not have a valid account with the provider, the user account does not enable access to the type of resources specified in the request, or another such reason is preventing the user from obtaining access to such resources, a communication can be sent to the user to enable the user to create or modify an account, or change the resources specified in the request, among other such options.

Once the user is authenticated, the account verified, and the resources allocated, the user can utilize the allocated resource(s) for the specified capacity, amount of data transfer, period of time, or other such value. In at least some embodiments, a user might provide a session token or other such credentials with subsequent requests in order to enable those requests to be processed on that user session. The user can receive a resource identifier, specific address, or other such information that can enable the client device 702 to communicate with an allocated resource without having to communicate with the service manager 710, at least until such time as a relevant aspect of the user account changes, the user is no longer granted access to the resource, or another such aspect changes.

The service manager 710 (or another such system or service) in this example can also function as a virtual layer of hardware and software components that handles control functions in addition to management actions, as may include provisioning, scaling, replication, etc. The resource manager can utilize dedicated APIs in the interface layer 808, where each API can be provided to receive requests for at least one specific action to be performed with respect to the data environment, such as to provision, scale, clone, or hibernate an instance. Upon receiving a request to one of the APIs, a Web services portion of the interface layer can parse or otherwise analyze the request to determine the steps or actions needed to act on or process the call. For example, a Web service call might be received that includes a request to create a data repository.

An interface layer 708 in at least one embodiment includes a scalable set of user-facing servers that can provide the various APIs and return the appropriate responses based on the API specifications. The interface layer also can include at least one API service layer that in one embodiment consists of stateless, replicated servers which process the externally-facing user APIs. The interface layer can be responsible for Web service front end features such as authenticating users based on credentials, authorizing the user, throttling user requests to the API servers, validating user input, and marshalling or unmarshalling requests and responses. The API layer also can be responsible for reading and writing database configuration data to/from the administration data store, in response to the API calls. In many embodiments, the Web services layer and/or API service layer will be the only externally visible component, or the only component that is visible to, and accessible by, users of the control service. The servers of the Web services layer can be stateless and scaled horizontally as known in the art. API servers, as well as the persistent data store, can be spread across multiple data centers in a region, for example, such that the servers are resilient to single data center failures.

The various embodiments can be further implemented in a wide variety of operating environments, which in some cases can include one or more user computers or computing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network and any combination thereof. In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices such as random access memory (RAM) or read-only memory (ROM), as well as removable media devices, memory cards, flash cards, etc. Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information.

The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed. Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A computer-implemented method, comprising:

receiving text;

using a machine learning model to determine a set of classification probabilities for the text relative to a set of nine anchor points in a three-dimensional cube, wherein the set of classification probabilities for the text is computed using an output of a large language model fine-tuned on a multi-genre natural language inference (MNLI) dataset;

determining a sentiment score indicative of an emotional content of the text based, at least in part, upon a convex combination of values from the nine anchor points, using the set of classification probabilities for the text; and generating one or more predictions based on the sentiment score, wherein the one or more predictions are associated with a response to an administered therapy for treatment-resistant depression.

2. The computer-implemented method of claim 1, wherein the sentiment score includes arousal scores, valence scores, and confidence scores for individual pieces of the text.

3. A computing system, comprising:

a computing device processor; and a memory device including instructions that, when executed by the computing device processor, enable the computing system to:

receive text;

use a machine learning model to determine a set of classification probabilities for the text relative to a set of nine anchor points in a three-dimensional cube, wherein the set of classification probabilities for the text is computed using an output of a large language model fine-tuned on a multi-genre natural language inference (MNLI) dataset; and determine a sentiment score indicative of an emotional content of the text based, at least in part, upon a convex combination of values from the nine anchor points, using the set of classification probabilities for the text; and generate one or more predictions based on the sentiment score, wherein the one or more predictions are associated with a response to an administered therapy for treatment-resistant depression.

4. The computing system of claim 3, wherein the sentiment score includes arousal scores, valence scores, and confidence scores for individual pieces of the text.

5. The computing system of claim 3, wherein the instructions that, when executed by the computing device processor, enable the computing system to further comprise:

pass the text through a classifier;

compute probability values indicative of a probability that a string of text, of the text, is within a class of one or more classes;

separate the one or more classes into a set of lists corresponding to the set of nine anchor points; and generate weights for individual strings of text based, at least in part, upon the set of lists.

6. A non-transitory computer-readable medium storing instructions that, when executed by at least one processor, cause the at least one processor to:

receive text;

use a machine learning model to determine a set of classification probabilities for the text relative to a set of nine anchor points in a three-dimensional cube, wherein the set of classification probabilities for the text is computed using an output of a large language model fine-tuned on a multi-genre natural language inference (MNLI) dataset; and determine a sentiment score indicative of an emotional content of the text based, at least in part, upon a convex combination of values from the nine anchor points, using the set of classification probabilities for the text; and generate one or more predictions based on the sentiment score, wherein the one or more predictions are associated with a response to an administered therapy for treatment-resistant depression.

7. The non-transitory computer-readable medium of claim 6, wherein the sentiment score includes arousal scores, valence scores, and confidence scores for individual pieces of the text.

8. The non-transitory computer-readable medium of claim 6, wherein the instructions, when executed by the at least one processor, cause the at least one processor to further comprise:

pass the text through a classifier;

compute probability values indicative of a probability that a string of text, of the set of text, is within a class of one or more classes;

separate the one or more classes into a set of lists corresponding to the set of nine anchor points; and generate weights for individual strings of text based, at least in part, upon the set of lists.

* * * * *